(12) United States Patent
Wang

(10) Patent No.: US 8,710,244 B2
(45) Date of Patent: Apr. 29, 2014

(54) DYES AND METHODS OF MARKING BIOLOGICAL MATERIAL

(71) Applicant: Industrial Technology Research Institute, Hsinchu (TW)

(72) Inventor: Shin-Shin Wang, Hsinchu (TW)

(73) Assignee: Industrial Technology Research Institute, Hsinchu (TW)

(*) Notice: Subject to any disclaimer, the term of this patent is extended or adjusted under 35 U.S.C. 154(b) by 0 days.

(21) Appl. No.: 13/728,859

(22) Filed: Dec. 27, 2012

(65) Prior Publication Data

US 2013/0344499 A1 Dec. 26, 2013

(30) Foreign Application Priority Data

Jun. 22, 2012 (TW) ............... 101122353 A

(51) Int. Cl.
*C07D 405/12* (2006.01)
*G01N 33/58* (2006.01)

(52) U.S. Cl.
CPC ............ *C07D 405/12* (2013.01); *G01N 33/582* (2013.01); *Y10S 436/80* (2013.01)
USPC .......................................... 548/525; 436/800

(58) Field of Classification Search
CPC ........................... C07D 405/12; G01N 33/582
USPC .......................................... 548/525; 436/800
See application file for complete search history.

(56) References Cited

U.S. PATENT DOCUMENTS

| | | | |
|---|---|---|---|
| 6,130,101 A * | 10/2000 | Mao et al. ..................... | 436/546 |
| 6,383,749 B2 | 5/2002 | Bochkariov et al. | |
| 6,448,407 B1 | 9/2002 | Lee et al. | |
| 6,649,769 B2 | 11/2003 | Lee et al. | |
| 6,750,357 B1 * | 6/2004 | Chiarello et al. ............ | 549/394 |
| 7,038,063 B2 | 5/2006 | Lee et al. | |
| 2006/0188915 A1 | 8/2006 | Lee et al. | |
| 2007/0254298 A1 | 11/2007 | Lee et al. | |
| 2010/0197030 A1 | 8/2010 | Mao et al. | |
| 2010/0209354 A1 | 8/2010 | Horcajada-Cortes et al. | |
| 2010/0226991 A1 | 9/2010 | Horcajada-Cortes et al. | |

FOREIGN PATENT DOCUMENTS

| | | |
|---|---|---|
| EP | 2 036 897 A1 | 3/2009 |
| WO | WO 2011/029459 A8 | 3/2011 |

OTHER PUBLICATIONS

Boyarskiy et al., "Photostable, Amino Reactive and Water-Soluble Fluorescent Labels Based on Sulfonated Rhodamine with a Rigidized Xanthene Fragment", Chemistry a European Journal, 2008, 14, pp. 1784-1792.

(Continued)

*Primary Examiner* — Robert Havlin
(74) *Attorney, Agent, or Firm* — Birch, Stewart, Kolasch & Birch, LLP

(57) ABSTRACT

Disclosed is a dye having the chemical formula:

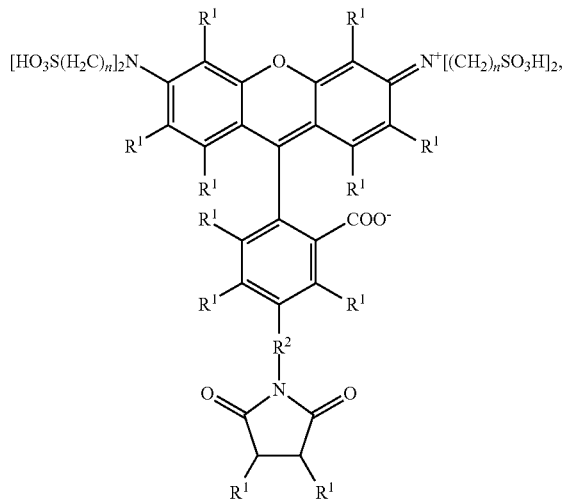

Formula I

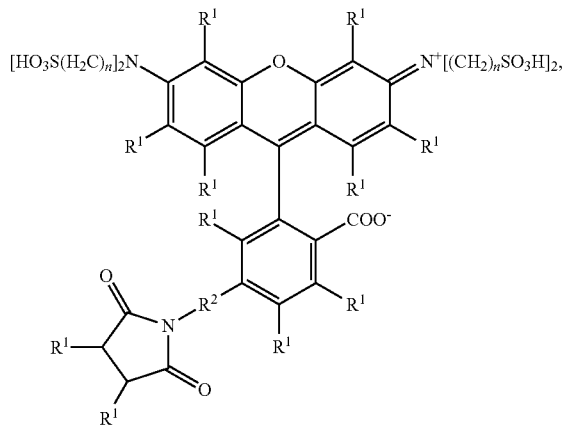

Formula II or a mixture thereof. Each $R^1$ is independently selected from hydrogen, halogen, cyano, alkyl, alkenyl, alkynyl, alkoxyl, alkylthio, alkylamino, dialkylamino, alkylaminocarbonyl, dialkylaminocarbonyl, aryl, heteroaryl, phosphoric acid, or sulfonic acid. Each $R^2$ is independently selected from

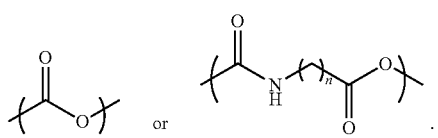

Each n is independently selected from an integer of 2 to 10.

9 Claims, 1 Drawing Sheet

(56) References Cited

OTHER PUBLICATIONS

Liu et al., "Rational design and synthesis of a novel class of highly fluorescent rhodamine dyes that have strong absorption at long wavelengths", Tetrahedron Letters, 2003, 44, pp. 4355-4359.

Meng et al., "Synthesis of N-hydroxysuccinimidyl benzoate and its structural insight into labeling activity of fluorescent probes", Dyes and Pigments, 2007, 75, pp. 166-169.

Mujumdar et al., "Cyanine Dye Labeling Reagents Containing Isothiocyanate Groups", Cytometry, 1989, 10, pp. 11-19.

Shandura et al., "New heterocyclic analogues of rhodamines", Dyes and Pigments, 2007, 73, pp. 25-30.

* cited by examiner

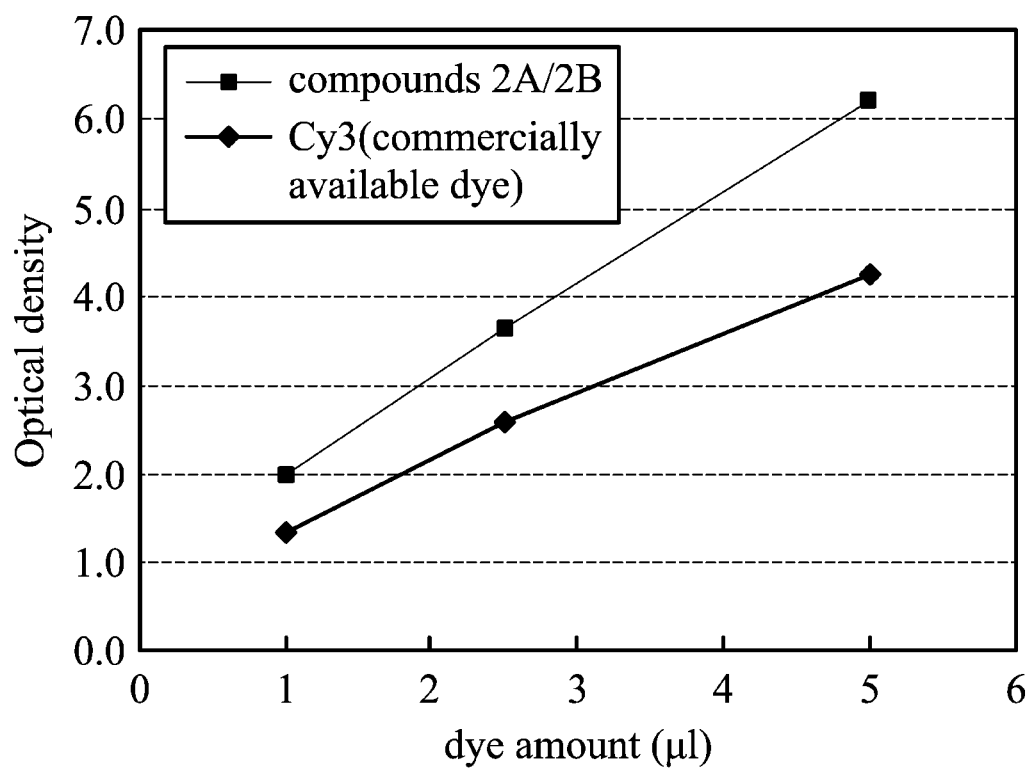

United States Patent US 8,710,244 B2

DYES AND METHODS OF MARKING BIOLOGICAL MATERIAL

CROSS REFERENCE TO RELATED APPLICATIONS

The present application is based on, and claims priority from, Taiwan Application Serial Number 101122353, filed on Jun. 22, 2012, the disclosure of which is hereby expressly incorporated by reference herein in its entirety.

TECHNICAL FIELD

The technical field relates to a dye, and in particular relates to a method of marking biological material with the dye.

BACKGROUND

Dyes are widely applied in biological research and medical diagnosis. The dyes may, in vivo or in vitro, mark biological material (such as amino acids, peptides, proteins, antibodies, biological polymers, cells, or tissues). If the dyes can be synthesized in great quantities to collocate with automatic inspection, the dyes can be used to mark biological material.

The Rhodamine dye family is one of current major dyes. However, the rhodamine structure is inherently water insoluble. As such, a hydrophilic group (e.g. sulfonic acid) should be grafted to the rhodamine structure to allow the rhodamine dye to dissolve in water for marking the biological material. A combination of factors, including the ratios of the concentrations between the dye and the biological material, the photoluminescence efficiency of the combination of the dye and the biological material, and method of grafting the sulfonic acid to the rhodamine structure should be simultaneously considered.

SUMMARY

One embodiment of the disclosure provides a dye, having the chemical formula:

Formula I

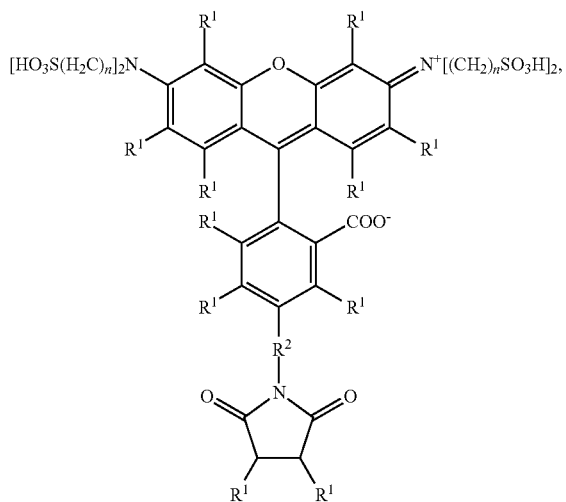

Formula II

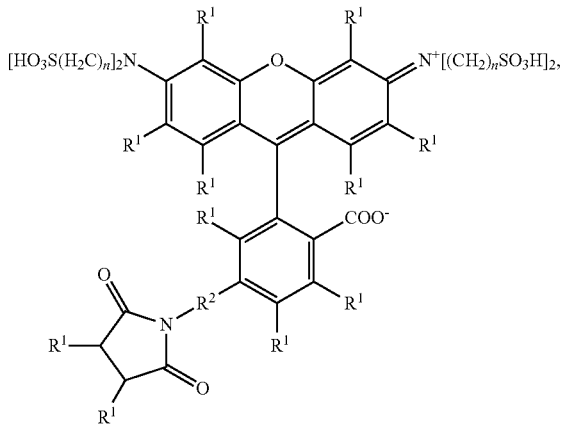

or mixtures thereof, wherein each $R^1$ is independently selected from hydrogen, halogen, cyano, alkyl, alkenyl, alkynyl, alkoxyl, alkylthio, alkylamino, dialkylamino, alkylaminocarbonyl, dialkylaminocarbonyl, aryl, heteroaryl, phosphoric acid, or sulfonic acid; each $R^2$ is independently selected from

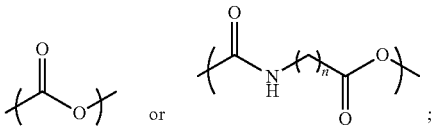

and each n is independently selected from an integer of 2 to 10.

One embodiment of the disclosure provides a method of marking biological material, comprising: mixing the biological material and the described dye, optionally at a pH of 7 to 9, such that the dye associates with the biological material; and providing an excitation light to the associated dye/biological material, and the associated dye emits a light.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

FIG. 1 shows a line chart of optical densities versus different amounts of different dyes combined with BSA.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The disclosure provides a dye capable of associating with the biological material having one or more peptide bonds, such as amino acids, peptides, proteins, antibodies, biological polymers, cells, tissues, or the like. As such, the dye can be utilized to mark the biological material. The dye has a terminal sulfonic acid group to be dissolved in water, and an N-succinimide ester group to be easily bound to the peptide bond. In one embodiment, the dye is first mixed with the biological material to be marked. Afterward, the dye associates with the biological material. The phrase "associates with" includes binding (covalently, ionically, or through hydrogen bonds), complexing with, or another relationship which keeps the dye and biological material in sufficiently close proximity to a target material so that the biological material of interest can be identified either by the presence or absence of dye. In another embodiment, the associated dye and the biological material is exposed to an excitation light (e.g. a UV light or a visible light), and the dye emits a light (e.g. a visible light) to mark the biological material. The marking method can be applied to mark the biological material in vivo or in vitro. For example, the dye has a chemical formula:

Formula I

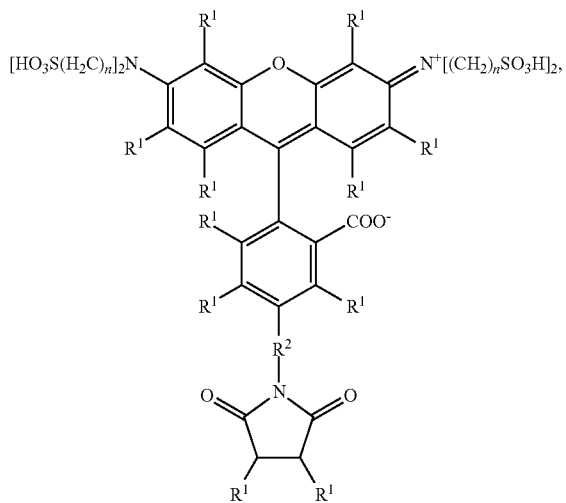

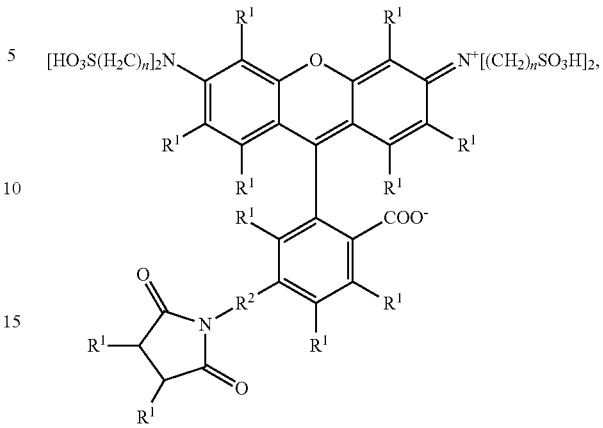

Formula II or mixtures thereof, wherein each $R^1$ is independently selected from hydrogen, halogen, cyano, alkyl, alkenyl, alkynyl, alkoxyl, alkylthio, alkylamino, dialkylamino, alkylaminocarbonyl, dialkylaminocarbonyl, aryl, heteroaryl, phosphoric acid, or sulfonic acid; each $R^2$ is independently selected from

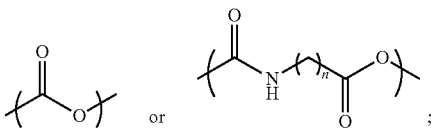

and each n is independently selected from an integer of 2 to 10.

In some embodiments, the dye is synthesized as below. Note that one skilled in the art may synthesize the dye through other ways and is not limited to following methods.

First, a cyclization is performed as shown in Reaction 1.

(Reaction 1)

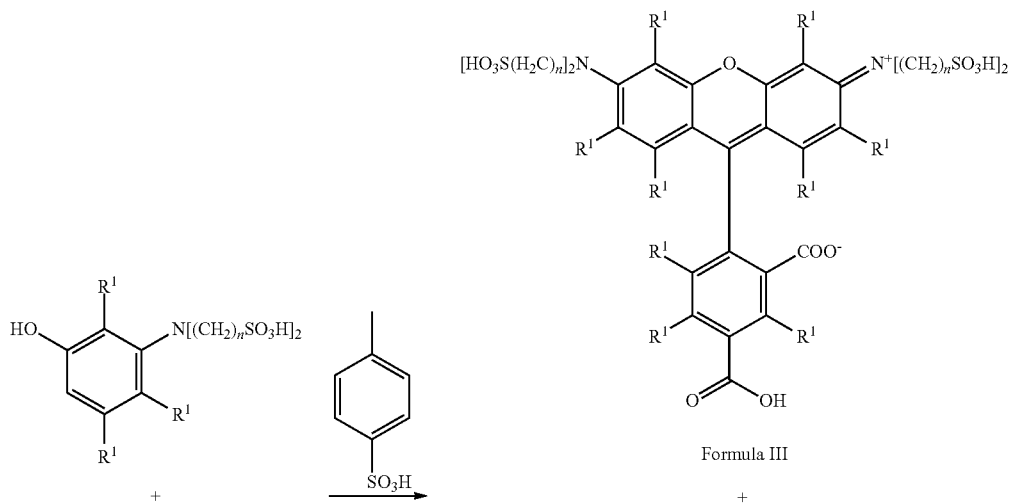

Formula III

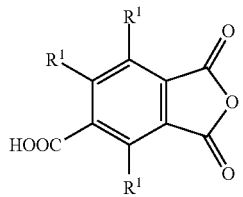
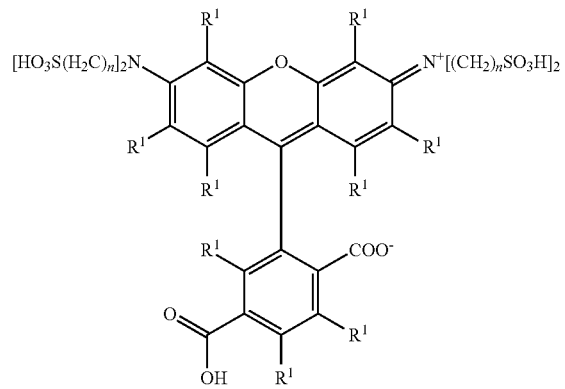
Formula IV
Thereafter, the product in Reaction 1 and N-hydroxysuccinimide are reacted as shown in Reaction 2, and the product thereof is a dye.
(Reaction 2)
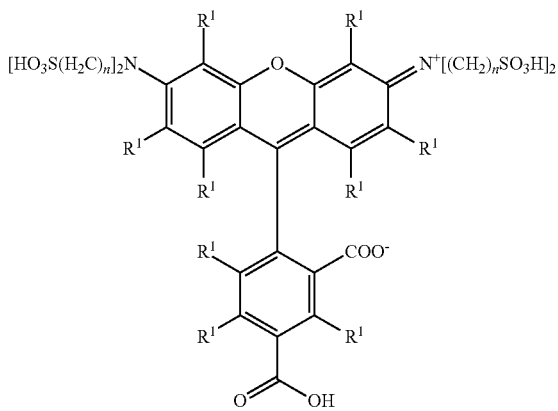
Formula III
+
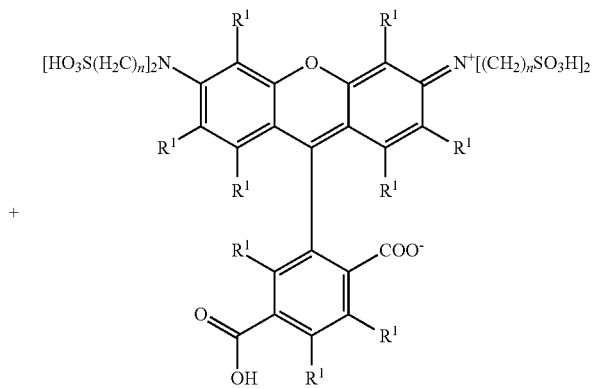
Formula IV
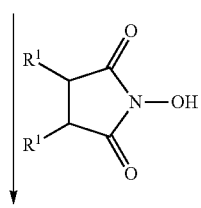

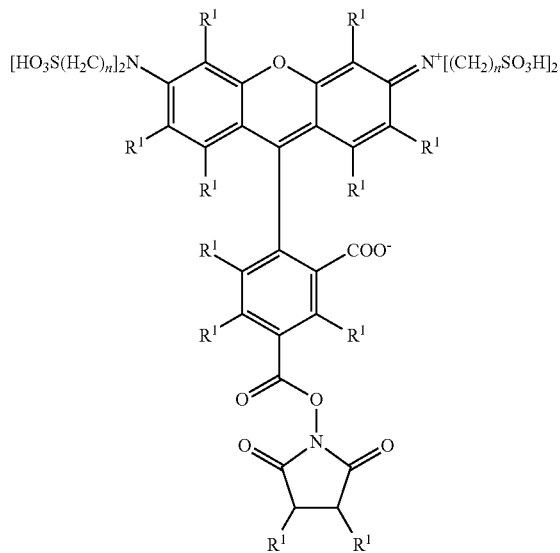

Formula V

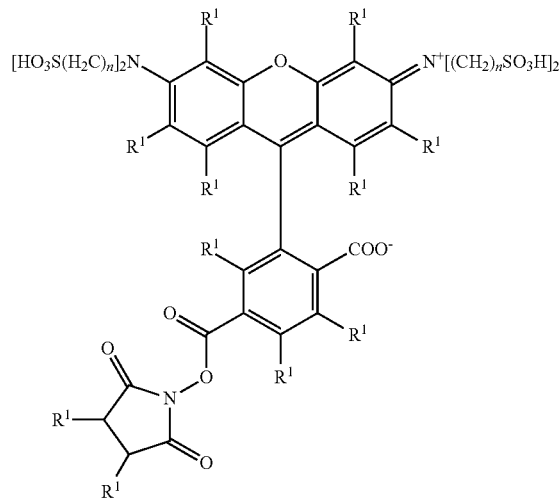

Formula VI

In Reactions 1 and 2, each $R^1$ is independently selected from hydrogen, halogen, cyano, alkyl, alkenyl, alkynyl, alkoxyl, alkylthio, alkylamino, dialkylamino, alkylaminocarbonyl, dialkylaminocarbonyl, aryl, heteroaryl, phosphoric acid, or sulfonic acid. Each n is independently selected from an integer of 2 to 10, or an integer of 3 to 6.

In another embodiment, the product in Reaction 1, N-hydroxysuccinimide, and amino acid are reacted as shown in Reaction 3, and the product thereof is a dye.

(Reaction 3)

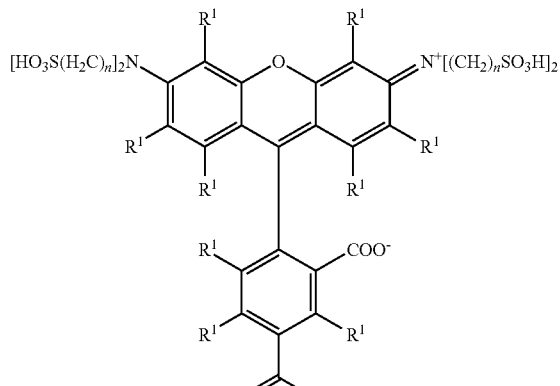

Formula III

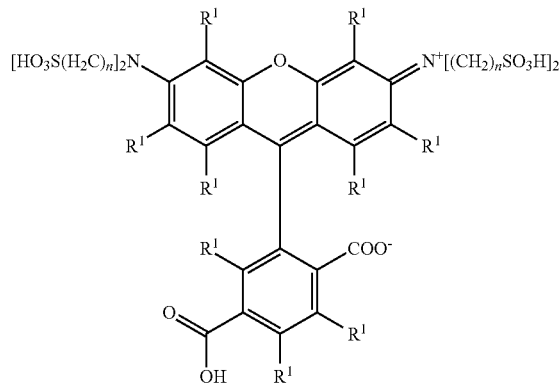

Formula IV

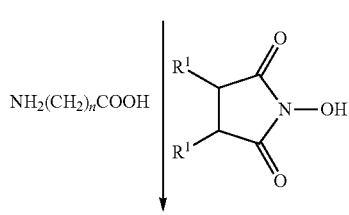

-continued

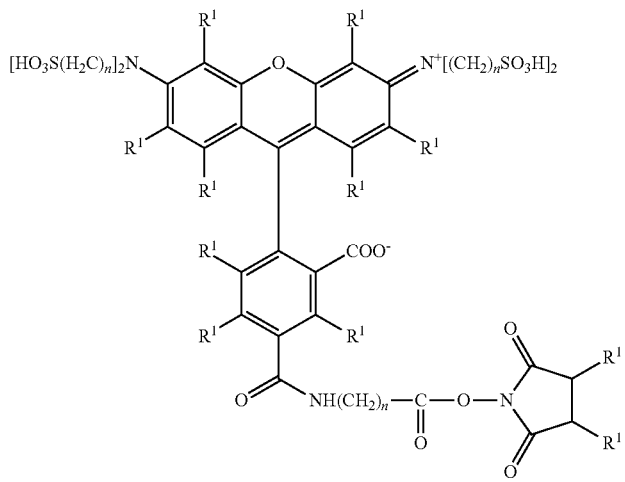

Formula VII

+

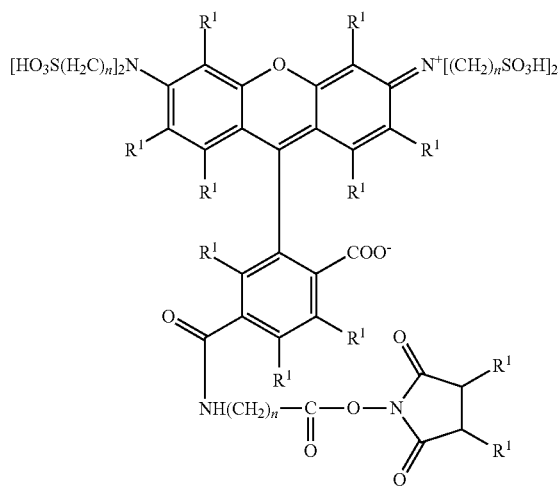

Formula VIII

In Reaction 3, each $R^1$ is independently selected from hydrogen, halogen, cyano, alkyl, alkenyl, alkynyl, alkoxyl, alkylthio, alkylamino, dialkylamino, alkylaminocarbonyl, dialkylaminocarbonyl, aryl, heteroaryl, phosphoric acid, or sulfonic acid. Each n is independently selected from an integer of 2 to 10, or an integer of 3 to 6.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Synthesis Example 1 Synthesis of N,N-dibutylsulfonate-1-phenol 2.0 g of compound A (0.0076 mmole), 1.5 mL of 1,4-butane sultone, 2.3 mL of triethylamine, and 10 mL of acetonitrile were put into a reaction bottle (100 mL). The mixture was heated to 60° C. for 20 hours, as shown in Reaction 4. The reaction was cooled and then vacuumed to remove the solvents thereof, thereby obtaining the compound B. The synthesis of the compound A can be referred to in Chemistry and Industry, 20, 345 (1974).

(Reaction 4)

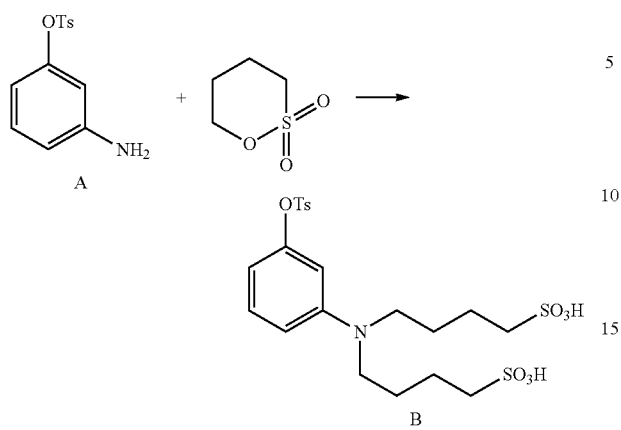

The compound B, 0.9576 g of LiOH.H$_2$O, 10 mL of methanol, and 10 mL of water were put into a reaction bottle (100 mL). The mixture was heated to 60° C. for 3 hours. The reaction was neutralized by hydrochloric acid to precipitate a solid, and then filtered to collect 3.04 g of the solid (compound C), as shown in Reaction 5.

(Reaction 5)

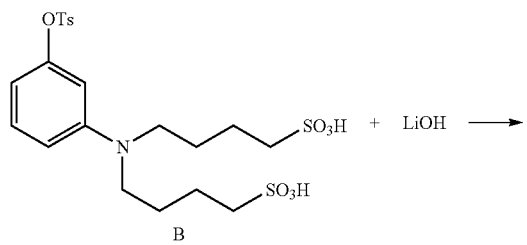

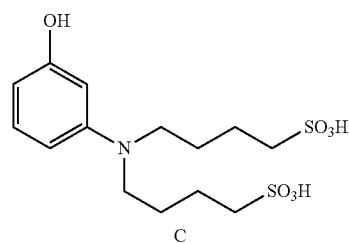

Example 1

Synthesis of Dye 3 g of the compound C, 0.9827 g of 1,2,4-benzenetricarboxylic anhydride (0.0051 mmole, commercially available from TCI AMERICA), 0.1495 g of p-toluenesulfonic acid, and 5 mL of propionic acid were put into a reaction bottle (100 mL).

The mixture was heated to 140° C. for 22 hours, as shown in Reaction 6. The reaction was cooled to room temperature, and then purified by column chromatography to obtain compounds 1A and 1B (totally 2.5383 g, yield=35%). The spectra data of the compounds 1A and 1B is as follows. $^1$H NMR (MeOH-d$_4$), δ=8.35(d, J=6 Hz, 1H), 8.27(s, 1H), 7.46(d, J=6 Hz, 1H), 7.16(d, J=6 Hz, 2H), 7.07(d, J=6 Hz, 2H), 7.00(s, 2H), 3.66(m, 8H), 2.88(m, 8H), 1.89(m, 16H).

(Reaction 6)

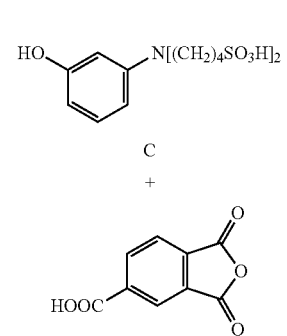

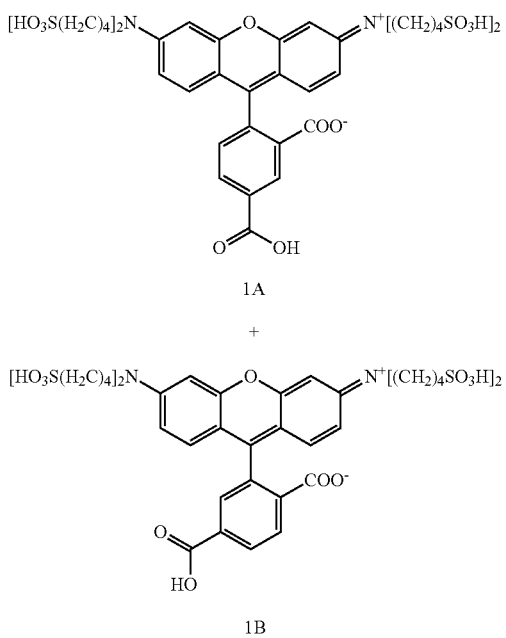

70 mg of the mixture of the compounds 1A and 1B (0.76 mmole), 35.6 mg of 1-(3-dimethylaminopropyl)-3-ethylcarbodiimide hydrochloride (EDC-HCl, 0.186 mmole), 19.71 mg of N-hydroxysuccinimide (0.171 mmole), and 4 mL of methanol were put into a reaction bottle (100 mL). The mixture was stirred and reacted at room temperature for 1 hour. The reaction was purified by column chromatography to obtain compounds 2A and 2B (totally 77.22 mg, yield=76.2%). The spectra data of the compounds 2A and 2B is as follows. $^1$H NMR (MeOH-d$_4$), δ=8.40(d, J=3 Hz, 1H), 8.35(s, 1H), 8.02(d, J=3 Hz, 1H), 7.08(m, 6H), 3.66(m, 8H), 2.88(m, 8H), 2.73(s, 4H), 1.89(m, 16H). An aqueous solution of the compounds 2A and 2B was analyzed by UV-VIS and fluorescent spectroscopy to measure its maximum absorption wavelength, maximum emission wavelength, and quantum yield, as tabulated in Table 1. A higher quantum yield results in a brighter light emission. The quantum yield of Cy3 is 0.15, which is far lower than the embodiments.

Example 2

Synthesis of Dye 60 mg of the mixture of the compounds 1A and 1B (0.0655 mmole), 15 mg of EDC-HCl (0.0786 mmole), and 4 mL of methanol were put into a reaction bottle (100 mL) to be stirred at room temperature for 1 hour. Afterward, 0.0172 g of 6-aminohexanoic acid (0.0172 mmole) was added into the reaction bottle to react at room temperature for 1 hour. 19.71 mg of N-hydroxysuccinimide (0.171 mmole) was then added into the reaction bottle to react at room temperature for 1 hour, as shown in Reaction 8. The reaction was purified by column chromatography to obtain compounds 3A and 3B (totally 18.70 mg, yield=25%). The spectra data of the compounds 3A and 3B is as follows. $^1$H NMR (MeOH-d$_4$), δ=8.30m, 2H), 7.41(m, 2H), 7.06(m, 5H), 3.68(m, 8H), 2.87(m, 10H), 2.74 (s, 4H), 2.19(m, 2H), 1.85(m, 18H), 1.64(m, 4H). An aqueous (Reaction 7)

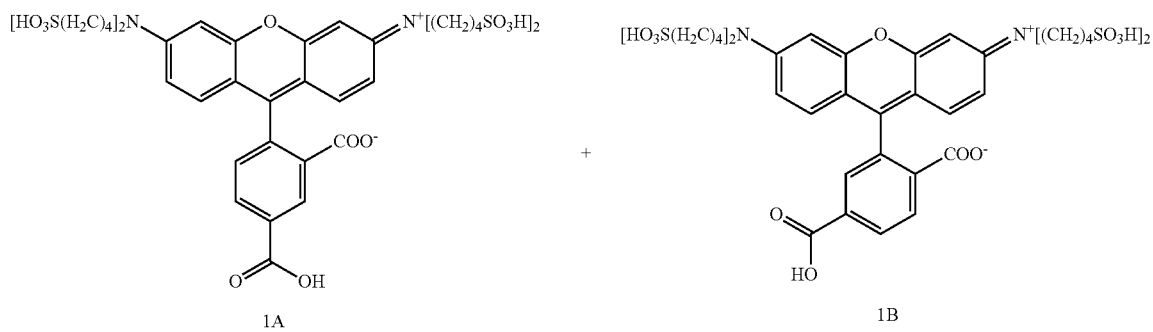

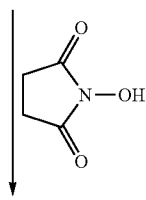

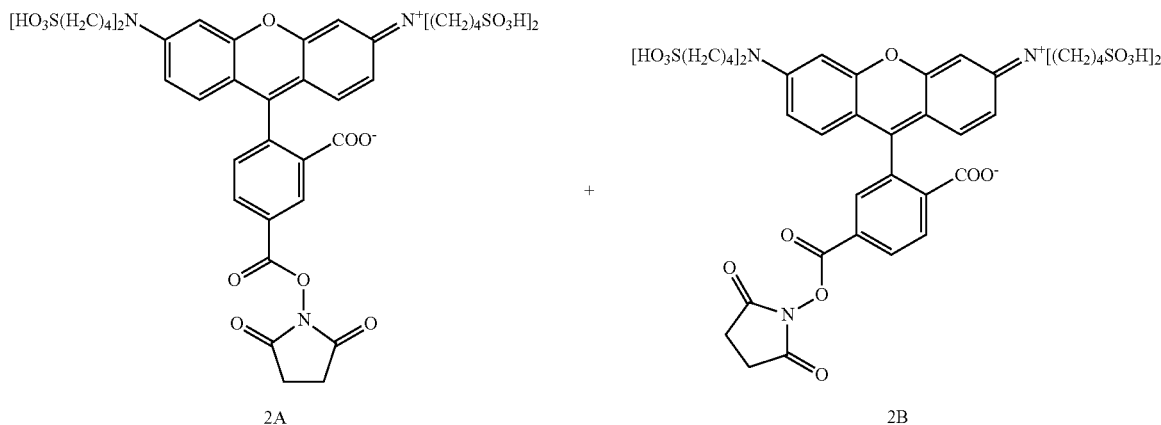

solution of the compounds 3A and 3B was analyzed by UV-VIS and fluorescent spectroscopy to measure its maximum absorption wavelength, maximum emission wavelength, and quantum efficiency, as tabulated in Table 1.
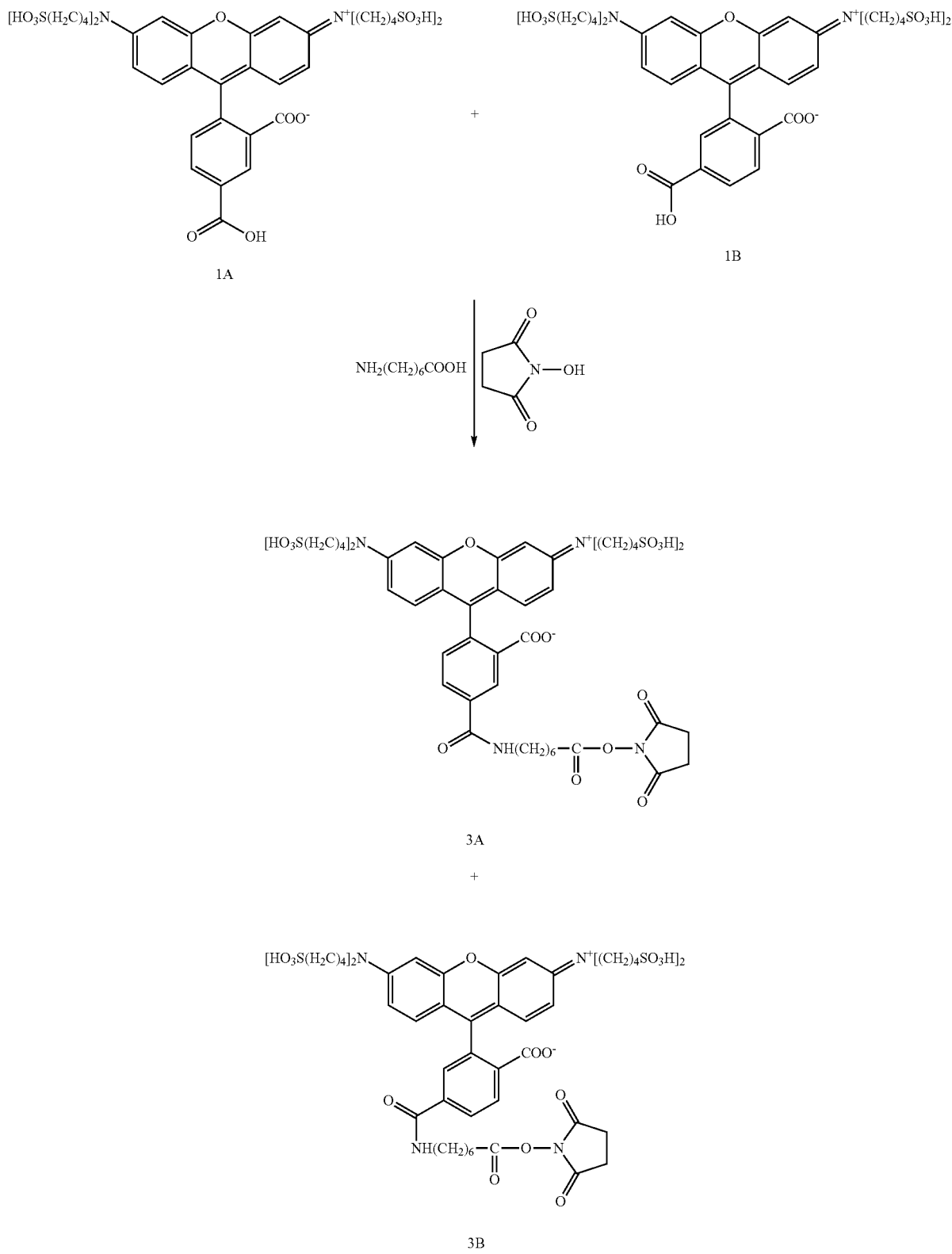

Example 3

Synthesis of Dye Precursor 3 g of N,N-dipropylsulfonate-1-phenol (0.01 mole), 1.4606 g of 1,2,4-benzenetricarboxylic anhydride (0.0076 mmole), 0.1112 g of p-toluenesulfonic acid (0.00058 mmole), and 5 mL of propionic acid were put into a reaction bottle (100 mL). The mixture was heated to 140° C. for 22 hours, as shown in reaction 6. The reaction was cooled to room temperature, and then purified by column chromatography to obtain compounds 4A and 4B (totally 1.8972 g, yield=35%). The spectra data of the compounds 4A and 4B is as follows. $^1$H NMR (MeOH-$d_4$), δ=8.38(d, J=6 Hz, 1H), 8.17(s, 1H), 7.53(d, J=6 Hz, 1H), 7.18(m, 41-1), 6.85(s, 2H), 3.84(m, 8H), 2.87(m, 8H), 2.19(m, 8H).

pH=8.5) were added to the 6 tubes, respectively. The compositions in the 6 tubes are listed in Table 2.

TABLE 2

| | No. | | | | | |
|---|---|---|---|---|---|---|
| Composition | A1 | A2 | A3 | B1 | B2 | B3 |
| Cy3 | 1 μL | 2.5 μL | 5 μL | 0 | 0 | 0 |
| Compounds 2A/2B | 0 | 0 | 0 | 1 μL | 2.5 μL | 5 μL |
| Sodium hydrocarbonate aqueous solution | 9 μL | 7.5 μL | 5 μL | 9 μL | 7.5 μL | 5 μL |
| 5% BSA solution | 10 μL | 10 μL | 10 μL | 10 μL | 10 μL | 10 μL |

The 6 compositions in the 6 tubes were evenly mixed, respectively, and then stood at room temperature for 1 hour.

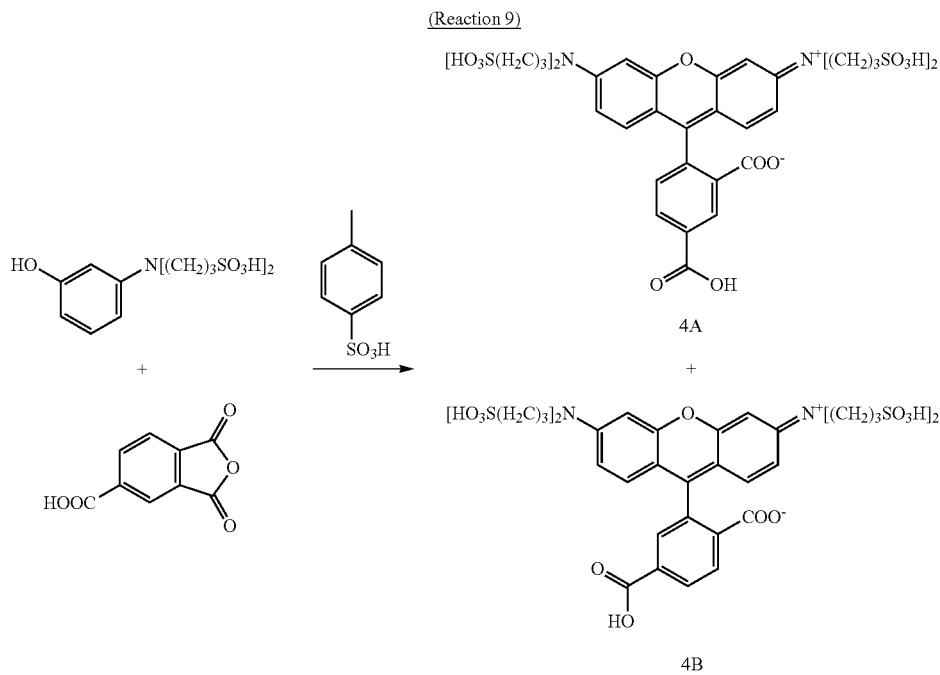

(Reaction 9)

TABLE 1

| Compound | Maximum absorption wavelength | Maximum emission wavelength | Quantum yield |
|---|---|---|---|
| Compound 2A (2B) | 562 nm | 595 nm | 1.45 |
| Compound 3A (3B) | 560 nm | 593 nm | 1.40 |

Example 4

The mixture of compounds 2A and 2B was dissolved in 2 μL of water, and the optical density (OD) of this aqueous solution was measured. The dye Cy3 (commercially available from GE Healthcare) was dissolved in 2 μL of water, and the OD of this aqueous solution was measured. The aqueous solution of compounds 2A/2B and the aqueous solution of Cy3 were tuned to the same concentration according to their OD. 10 μL of 5% bovine serum albumin solution (BSA solution) was added to 6 tubes (1.5 mL), respectively. Different amounts of the aqueous solutions of the dye Cy3, the compounds 2A/2B, and sodium hydrocarbonate (100 mM, The bound dye and the BSA, the unbound dye, and the unbound BSA were separated by size-exclusive chromatography. 9 μL of water was added to 1 μL of the separated bound dye and the BSA, and the full-wavelength OD of the solution was measured to check the marking effect of the sample. FIG. 1 shows a line chart of optical densities versus different amounts of different dyes in the samples of the 6 tubes. As shown in FIG. 1, the compounds 2A and 2B have a significantly better marking effect (compared with the marking effect of the commercially available dye Cy3). The compounds 2A/2B had a higher quantum yield than the commercially available dye Cy3.

As shown in Examples, the dye has following properties. (1) The dye produces a strong fluorescent signal after associating with the biological material. (2) The dye has stable absorption and emission wavelengths after associating with the biological material.

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. A dye, having the chemical formula:

Formula I

[structure: xanthene dye with $[HO_3S(H_2C)_n]_2N$ and $N^+[(CH_2)_nSO_3H]_2$ substituents, $R^1$ groups, COO⁻, and pendant $R^2$-linked maleimide/succinimide group with $R^1$ substituents]

Formula II

[structure: similar xanthene dye with $[HO_3S(H_2C)_n]_2N$ and $N^+[(CH_2)_nSO_3H]_2$ substituents, $R^1$ groups, COO⁻, and $R^2$-linked succinimide group]

or mixtures thereof, wherein each $R^1$ is independently selected from hydrogen, halogen, cyano, alkyl, alkenyl, alkynyl, alkoxyl, alkylthio, alkylamino, dialkylamino, alkylaminocarbonyl, dialkylaminocarbonyl, aryl, heteroaryl, phosphoric acid, or sulfonic acid;

each $R^2$ is independently selected from

[two linker structures shown: a carbonate-type $-C(=O)-O-$ linker, or an amide-ester linker $-C(=O)-NH-(CH_2)_n-O-C(=O)-$]

and each n is independently selected from an integer of 2 to 10.

2. The dye as claimed in claim 1, having the chemical formula:

Formula V

[structure: xanthene dye with $[HO_3S(H_2C)_n]_2N$ and $N^+[(CH_2)_nSO_3H]_2$ substituents, COO⁻ and NHS ester group with $R^1$ substituents on succinimide]

Formula VI

[structure: xanthene dye with $[HO_3S(H_2C)_n]_2N$ and $N^+[(CH_2)_nSO_3H]_2$ substituents, COO⁻ and NHS ester linkage with $R^1$ substituents]

or mixtures thereof.

3. The dye as claimed in claim 2, having the chemical formula:

2A

[structure: xanthene dye with $[HO_3S(H_2C)_4]_2N$ and $N^+[(CH_2)_4SO_3H]_2$ substituents, COO⁻, and NHS ester]

-continued

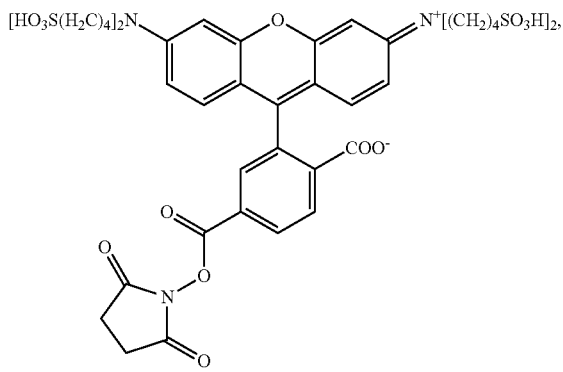

or mixtures thereof.

4. The dye as claimed in claim 1, having the chemical formula:

Formula VII

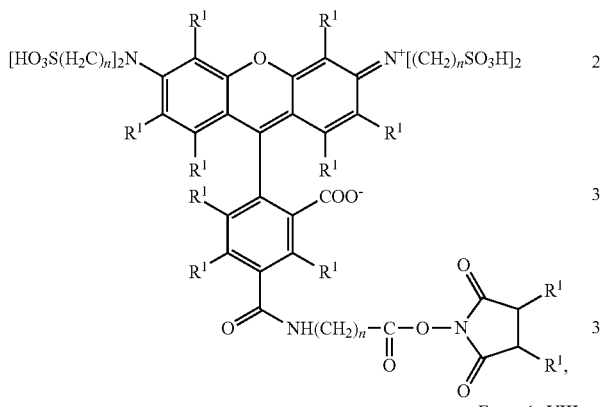

Formula VIII

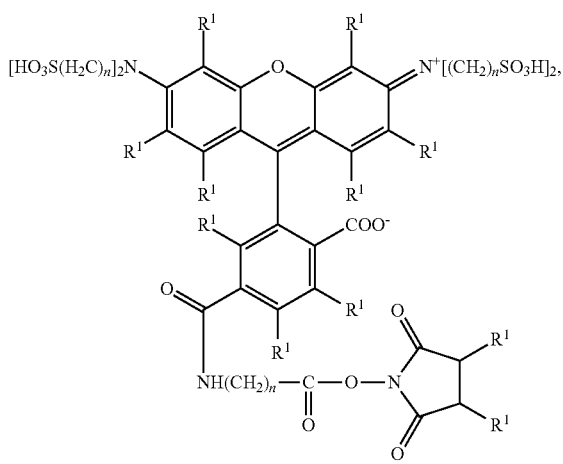

or mixtures thereof.

5. The dye as claimed in claim 4, having the chemical formula:

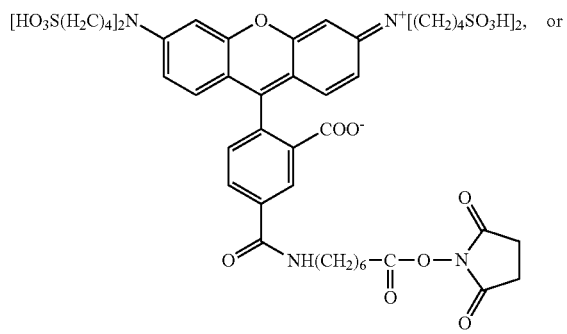

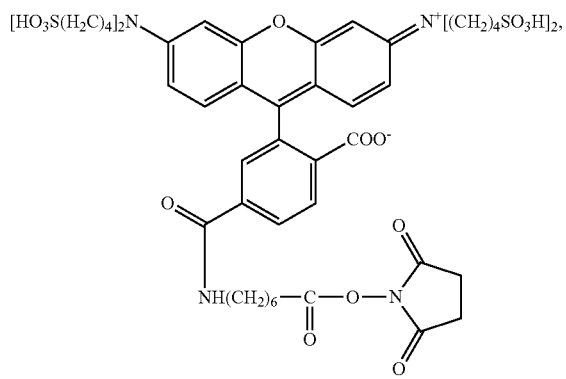

or mixtures thereof.

6. A method of marking biological material, comprising:
   mixing biological material and the dye of claim 1, such that the dye associates with the biological material; and
   providing an excitation light to the associated biological material, and the associated dye emits a light.

7. The method of claim 6, wherein the biological material and dye is mixed at a pH of 7 to 9.

8. The method as claimed in claim 6, wherein the excitation light comprises UV light or visible light.

9. The method as claimed in claim 6, wherein the biological material comprises one or more amino acids, peptides, proteins, antibodies, biological polymers, cells, or tissues.

* * * * *